(12) United States Patent
Yardimci et al.

(10) Patent No.: US 7,988,768 B2
(45) Date of Patent: Aug. 2, 2011

(54) DIALYSIS SYSTEMS HAVING SPIRALING FLUID AIR SEPARATION CHAMBERS

(75) Inventors: Atif M. Yardimci, Vernon Hills, IL (US); James C. Laird, Grayslake, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 12/979,764

(22) Filed: Dec. 28, 2010

(65) Prior Publication Data

US 2011/0092895 A1 Apr. 21, 2011

Related U.S. Application Data

(63) Continuation of application No. 11/865,552, filed on Oct. 1, 2007, now Pat. No. 7,871,462.

(51) Int. Cl.
*B01D 19/00* (2006.01)
(52) U.S. Cl. ............... 95/261; 95/262; 96/204; 96/215; 96/207; 96/208
(58) Field of Classification Search .............. 95/262, 95/260, 261; 96/204, 220, 215, 207, 208
See application file for complete search history.

(56) References Cited

U.S. PATENT DOCUMENTS

| | | | |
|---|---|---|---|
| 250,868 A | 12/1881 | Abbott | |
| 927,476 A | 7/1909 | Barker | |
| 1,505,050 A | 8/1924 | Lauritsen | |
| 2,292,007 A | 8/1942 | Morgan | |
| 3,044,236 A | 7/1962 | Bearden et al. | |
| 3,074,645 A | 1/1963 | Main | |
| 3,095,062 A | 6/1963 | Neely | |
| 3,229,445 A | 1/1966 | Kraft | |
| 3,287,885 A | 11/1966 | Sommer | |
| 3,295,297 A | 1/1967 | Collins | |
| 3,342,019 A | 9/1967 | Smythe | |
| 3,412,760 A | 11/1968 | Franck | |
| 3,527,572 A | 9/1970 | Urkiewicz | |
| 3,581,464 A | 6/1971 | Bhuta et al. | |
| 3,598,727 A | 8/1971 | Wilock | |
| 3,677,710 A | 7/1972 | Hirsch | |
| 3,744,492 A | 7/1973 | Leibinsohn | |
| 3,769,207 A | 10/1973 | Baer | |
| 3,771,288 A | 11/1973 | Wisman et al. | |
| 3,795,088 A | 3/1974 | Esmond | |
| 3,827,561 A | 8/1974 | Serfass et al. | |
| 3,834,386 A | 9/1974 | Sisley | |
| 3,849,071 A | 11/1974 | Kayser | |
| 3,908,653 A | 9/1975 | Kettering | |
| 3,964,479 A | 6/1976 | Boag et al. | |

(Continued)

FOREIGN PATENT DOCUMENTS

CH 296007 1/1954

(Continued)

*Primary Examiner* — Duane Smith
*Assistant Examiner* — Douglas Theisen
(74) *Attorney, Agent, or Firm* — K&L Gates LLP

(57) ABSTRACT

A dialysis fluid cassette includes a rigid portion defining at least one valve chamber, the rigid portion further defining an air separation chamber, the air separation chamber when in an operating position including an inner surface, a fluid inlet and a fluid outlet and configured to cause a dialysis fluid to spiral around the inner surface toward the fluid outlet, such that air is removed from the dialysis fluid.

20 Claims, 10 Drawing Sheets

U.S. PATENT DOCUMENTS

| | | | | |
|---|---|---|---|---|
| 3,976,311 A | | 8/1976 | Spendlove | |
| 3,985,134 A | | 10/1976 | Lissot et al. | |
| 3,996,027 A | * | 12/1976 | Schnell et al. | 95/261 |
| 4,031,891 A | | 6/1977 | Jess | |
| 4,038,190 A | | 7/1977 | Baudet et al. | |
| 4,047,563 A | | 9/1977 | Kurata | |
| 4,048,995 A | | 9/1977 | Mittleman | |
| 4,054,522 A | | 10/1977 | Pinkerton | |
| 4,061,031 A | | 12/1977 | Grimsrud | |
| 4,102,655 A | | 7/1978 | Jeffrey et al. | |
| 4,137,160 A | * | 1/1979 | Ebling et al. | 95/259 |
| 4,149,860 A | | 4/1979 | Kulik | |
| 4,151,088 A | | 4/1979 | Wolf, Jr. et al. | |
| 4,191,182 A | | 3/1980 | Popovich et al. | |
| 4,200,095 A | | 4/1980 | Reti | |
| 4,293,413 A | | 10/1981 | Schnell | |
| 4,304,670 A | | 12/1981 | Watanabe et al. | |
| 4,311,137 A | | 1/1982 | Gerard | |
| 4,325,715 A | | 4/1982 | Bowman et al. | |
| 4,344,777 A | | 8/1982 | Siposs | |
| 4,345,919 A | * | 8/1982 | Wilkinson et al. | 95/261 |
| 4,345,999 A | | 8/1982 | Sigdell et al. | |
| 4,353,368 A | | 10/1982 | Slovak et al. | |
| 4,363,641 A | | 12/1982 | Finn, III | |
| 4,368,118 A | | 1/1983 | Siposs | |
| 4,427,009 A | | 1/1984 | Wells et al. | |
| 4,433,971 A | | 2/1984 | Lindsay et al. | |
| 4,486,188 A | | 12/1984 | Altshuler et al. | |
| 4,493,705 A | | 1/1985 | Gordon et al. | |
| 4,512,163 A | | 4/1985 | Wells et al. | |
| 4,531,937 A | | 7/1985 | Yates | |
| 4,568,333 A | | 2/1986 | Sawyer et al. | |
| 4,583,981 A | | 4/1986 | Urquhart et al. | |
| 4,586,925 A | | 5/1986 | Carlsson et al. | |
| 4,622,032 A | | 11/1986 | Katsura et al. | |
| 4,643,713 A | | 2/1987 | Viitala | |
| 4,643,715 A | | 2/1987 | Isono et al. | |
| 4,666,598 A | | 5/1987 | Heath et al. | |
| 4,681,606 A | | 7/1987 | Swan, Jr. et al. | |
| 4,722,725 A | | 2/1988 | Sawyer et al. | |
| 4,722,731 A | | 2/1988 | Vailancourt | |
| 4,734,269 A | | 3/1988 | Clarke et al. | |
| 4,806,135 A | | 2/1989 | Siposs | |
| 4,932,987 A | | 6/1990 | Molina | |
| 4,941,875 A | | 7/1990 | Brennan | |
| 4,946,439 A | | 8/1990 | Eggers | |
| D311,061 S | | 10/1990 | Vrana et al. | |
| 4,976,685 A | | 12/1990 | Block, Jr. | |
| 4,997,464 A | | 3/1991 | Kopf | |
| 5,047,147 A | | 9/1991 | Chevallet et al. | |
| 5,049,492 A | | 9/1991 | Sauer et al. | |
| 5,059,173 A | | 10/1991 | Sacco | |
| 5,061,236 A | | 10/1991 | Sutherland et al. | |
| 5,061,365 A | | 10/1991 | Utterberg | |
| 5,112,480 A | | 5/1992 | Hukasawa | |
| 5,167,921 A | | 12/1992 | Gordon | |
| 5,178,763 A | | 1/1993 | Delaunay | |
| 5,204,000 A | | 4/1993 | Steadman et al. | |
| 5,228,889 A | | 7/1993 | Cortial et al. | |
| 5,246,560 A | | 9/1993 | Nekoksa et al. | |
| 5,268,077 A | | 12/1993 | Bubik et al. | |
| 5,328,461 A | | 7/1994 | Utterberg | |
| 5,356,376 A | | 10/1994 | Milijasevic et al. | |
| 5,358,481 A | | 10/1994 | Todd et al. | |
| 5,368,555 A | | 11/1994 | Sussman et al. | |
| 5,394,732 A | | 3/1995 | Johnson et al. | |
| 5,411,705 A | | 5/1995 | Thor et al. | |
| 5,421,815 A | | 6/1995 | Noguchi et al. | |
| 5,429,595 A | | 7/1995 | Wright, Jr. et al. | |
| 5,441,636 A | | 8/1995 | Chevallet et al. | |
| 5,468,388 A | | 11/1995 | Goddard et al. | |
| 5,489,385 A | | 2/1996 | Raabe et al. | |
| 5,503,801 A | | 4/1996 | Brugger | |
| 5,509,895 A | | 4/1996 | Noguchi et al. | |
| 5,520,640 A | | 5/1996 | Utterberg | |
| 5,578,070 A | | 11/1996 | Utterberg | |
| 5,591,251 A | | 1/1997 | Brugger | |
| 5,605,540 A | | 2/1997 | Utterberg | |
| 5,637,081 A | | 6/1997 | Noguchi et al. | |
| 5,643,205 A | | 7/1997 | Utterberg | |
| 5,650,071 A | | 7/1997 | Brugger et al. | |
| 5,674,199 A | | 10/1997 | Brugger | |
| 5,681,294 A | | 10/1997 | Osborne et al. | |
| 5,683,355 A | | 11/1997 | Fini et al. | |
| 5,730,730 A | | 3/1998 | Darling, Jr. | |
| 5,763,266 A | | 6/1998 | Palsson et al. | |
| 5,776,091 A | | 7/1998 | Brugger et al. | |
| 5,800,597 A | | 9/1998 | Perrotta et al. | |
| 5,830,185 A | | 11/1998 | Block, Jr. | |
| 5,849,065 A | * | 12/1998 | Wojke | 96/211 |
| 5,851,202 A | | 12/1998 | Carlsson | |
| 5,858,239 A | | 1/1999 | Kenley et al. | |
| 5,863,421 A | | 1/1999 | Peter, Jr. et al. | |
| 5,895,368 A | | 4/1999 | Utterberg | |
| 5,928,889 A | | 7/1999 | Bakich et al. | |
| 5,931,990 A | | 8/1999 | Andrews | |
| 5,951,870 A | | 9/1999 | Utterberg | |
| 5,980,741 A | | 11/1999 | Schnell et al. | |
| 5,983,947 A | | 11/1999 | Utterberg | |
| 5,989,318 A | | 11/1999 | Schroll | |
| 6,010,623 A | | 1/2000 | Schnell et al. | |
| 6,019,824 A | | 2/2000 | Schnell | |
| 6,046,806 A | | 4/2000 | Thompson | |
| 6,051,134 A | | 4/2000 | Schnell et al. | |
| 6,053,967 A | * | 4/2000 | Heilmann et al. | 96/208 |
| 6,066,111 A | | 5/2000 | Brockhoff | |
| 6,071,269 A | | 6/2000 | Schnell et al. | |
| 6,117,342 A | | 9/2000 | Schnell et al. | |
| 6,171,484 B1 | | 1/2001 | Schnell et al. | |
| 6,176,903 B1 | | 1/2001 | Wamsiedler | |
| 6,187,198 B1 | | 2/2001 | Utterberg | |
| 6,206,954 B1 | | 3/2001 | Schnell et al. | |
| 6,251,167 B1 | | 6/2001 | Berson | |
| 6,312,414 B1 | | 11/2001 | Brockhoff et al. | |
| 6,344,139 B1 | | 2/2002 | Utterberg | |
| 6,357,600 B1 | | 3/2002 | Scagliarini | |
| 6,391,541 B1 | | 5/2002 | Petersen et al. | |
| 6,391,638 B1 | | 5/2002 | Shaaltiel | |
| 6,464,878 B2 | | 10/2002 | Utterberg | |
| 6,481,455 B2 | | 11/2002 | Gustafson et al. | |
| 6,514,255 B1 | | 2/2003 | Ferree | |
| 6,517,732 B1 | * | 2/2003 | Brockoff et al. | 210/782 |
| 6,537,356 B1 | | 3/2003 | Soriano | |
| 6,562,107 B2 | | 5/2003 | Purdom et al. | |
| 6,755,801 B2 | | 6/2004 | Utterberg et al. | |
| 6,827,862 B1 | | 12/2004 | Brockhoff et al. | |
| 7,842,123 B2 | * | 11/2010 | Milo et al. | 95/30 |
| 2001/0042441 A1 | | 11/2001 | Purdom et al. | |
| 2004/0019313 A1 | | 1/2004 | Childers et al. | |
| 2009/0199708 A1 | * | 8/2009 | Milo et al. | 95/30 |

FOREIGN PATENT DOCUMENTS

| | | |
|---|---|---|
| DE | 1806654 | 5/1970 |
| EP | 0 058 325 | 8/1982 |
| EP | 0 106 026 | 4/1984 |
| EP | 0 143 340 | 6/1985 |
| EP | 0 318 993 | 6/1989 |
| EP | 0 350 675 | 1/1990 |
| EP | 0 501 144 | 1/1992 |
| EP | 0 587 251 | 3/1994 |
| EP | 0 776 222 | 4/2003 |
| GB | 1 408 319 | 10/1975 |
| GB | 1 554 810 | 10/1979 |
| GB | 2 061 755 | 5/1981 |
| GB | 2 212 739 | 8/1989 |
| WO | WO 98/23353 | 6/1998 |
| WO | WO 2006/120415 | 11/2006 |
| WO | WO 2008053287 A1 * | 5/2008 |

* cited by examiner

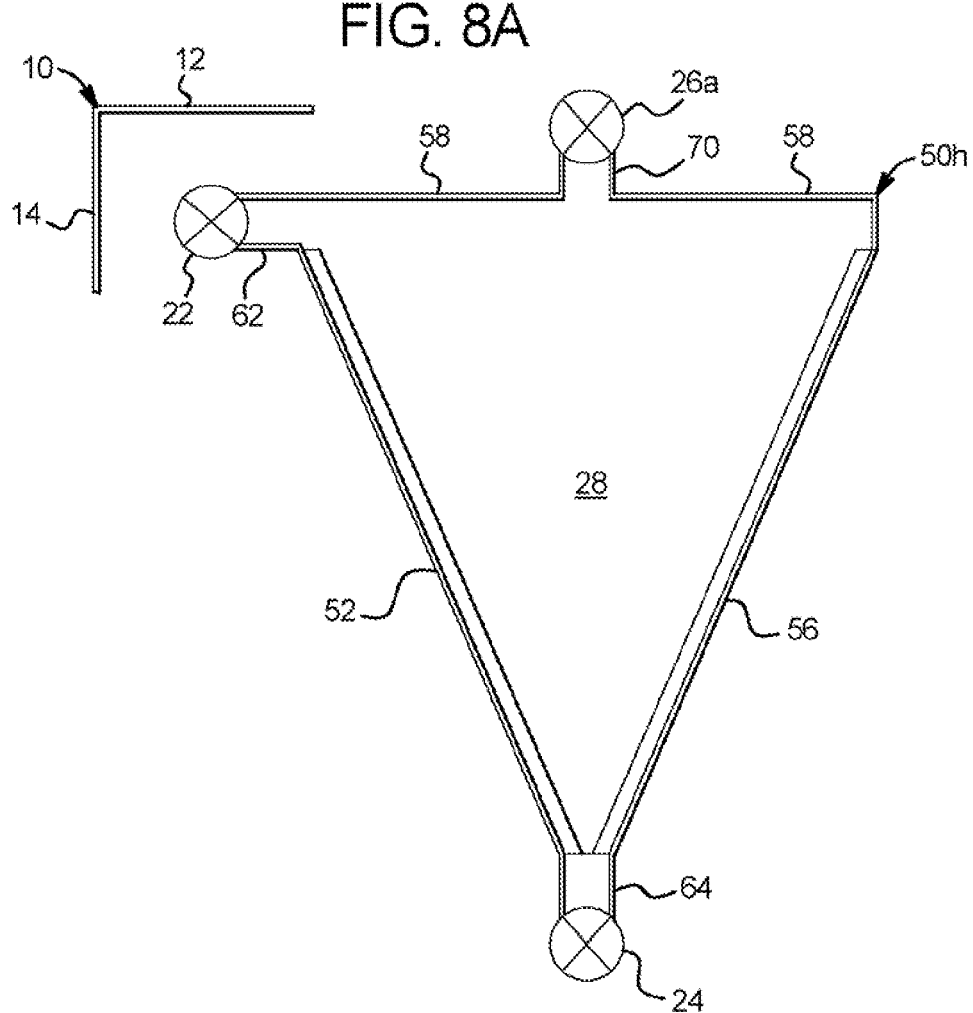
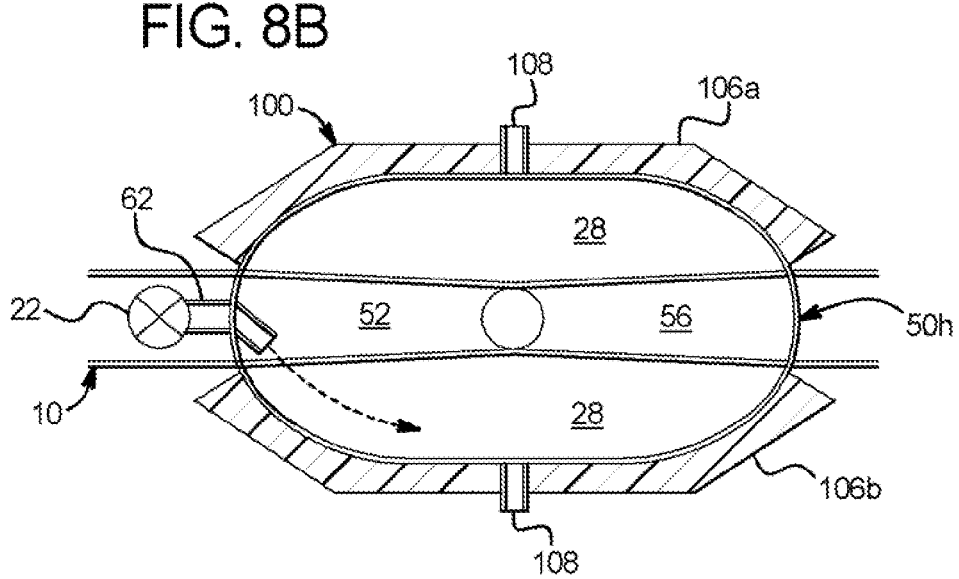

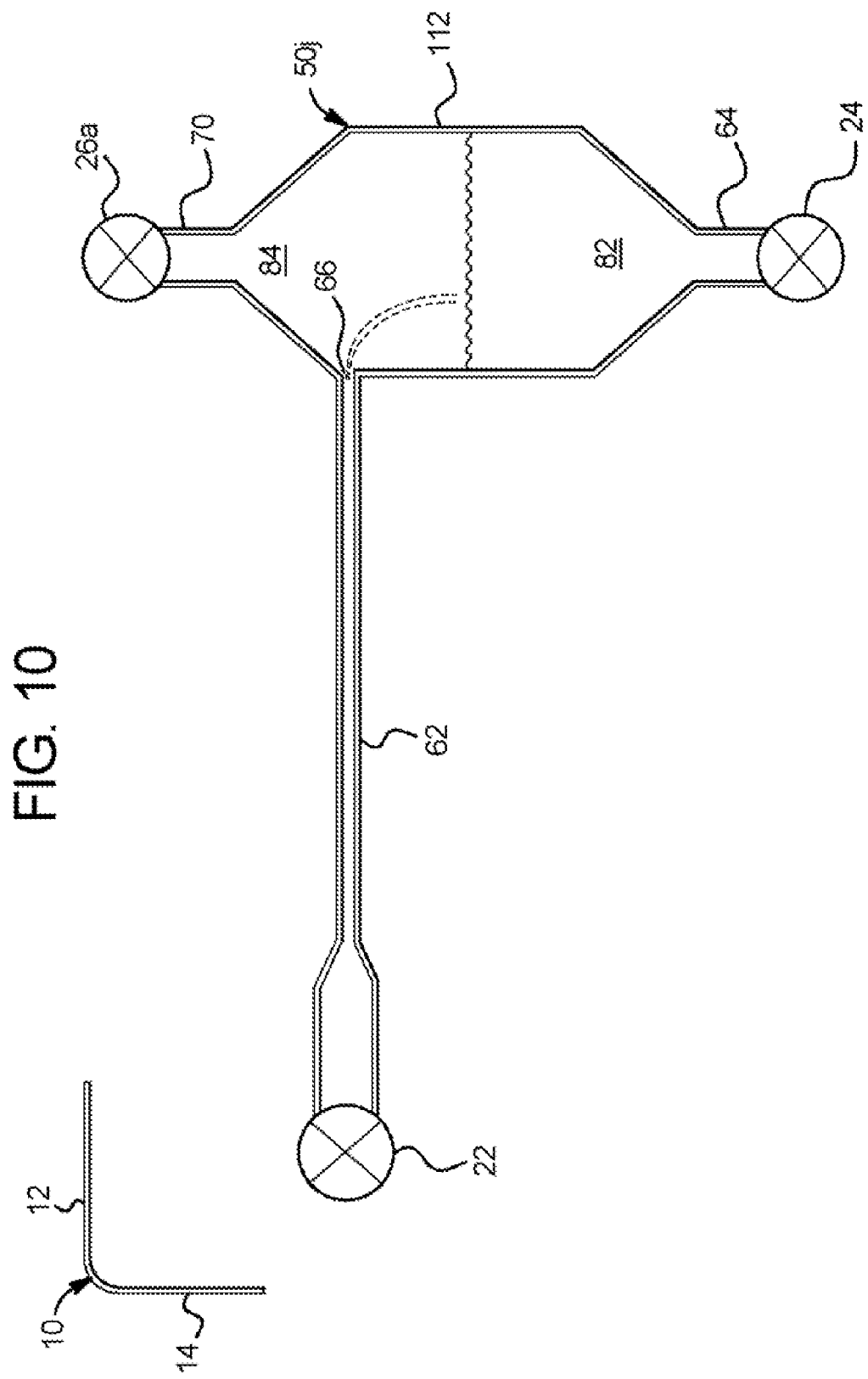

DIALYSIS SYSTEMS HAVING SPIRALING FLUID AIR SEPARATION CHAMBERS

PRIORITY CLAIM

This application is a continuation of, claims priority to and the benefit of U.S. patent application Ser. No. 11/865,552, filed Oct. 1, 2007, the entire contents of which are incorporated herein by reference and relied upon.

BACKGROUND

The examples discussed below relate generally to medical fluid delivery. More particularly, the examples disclose systems, methods and apparatuses for dialysis such as hemodialysis ("HD") automated peritoneal dialysis ("APD").

Due to various causes, a person's renal system can fail. Renal failure produces several physiological derangements. It is no longer possible to balance water and minerals or to excrete daily metabolic load. Toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that normal functioning kidneys would otherwise remove. Dialysis treatment for replacement of kidney functions is critical to many people because the treatment is life saving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate to cause diffusion. Hemofiltration ("HF") is an alternative renal replacement therapy that relies on a convective transport of toxins from the patient's blood. This therapy is accomplished by adding substitution or replacement fluid to the extracorporeal circuit during treatment (typically ten to ninety liters of such fluid). That substitution fluid and the fluid accumulated by the patient in between treatments is ultrafiltered over the course of the HF treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration ("HDF") is a treatment modality that combines convective and diffusive clearances. HDF uses dialysate flowing through a dialyzer, similar to standard hemodialysis, to provide diffusive clearance. In addition, substitution solution is provided directly to the extracorporeal circuit, providing convective clearance.

Most HD (HF, HDF) treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that a patient receiving more frequent treatments removes more toxins and waste products than a patient receiving less frequent but perhaps longer treatments. A patient receiving more frequent treatments does not experience as much of a down cycle as does an in-center patient who has built-up two or three days worth of toxins prior to a treatment. In certain areas, the closest dialysis center can be many miles from the patient's home causing door-to-door treatment time to consume a large portion of the day. HHD can take place overnight or during the day while the patient relaxes, works or is otherwise productive.

Another type of kidney failure therapy is peritoneal dialysis, which infuses a dialysis solution, also called dialysate, into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow dialysate and continuous flow peritoneal dialysis ("CFPD"). CAPD is a manual dialysis treatment. Here, the patient manually connects an implanted catheter to a drain to allow spent dialysate fluid to drain from the peritoneal cavity. The patient then connects the catheter to a bag of fresh dialysate to infuse fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter and into the patient's peritoneal cavity. APD machines also allow for the dialysate to dwell within the cavity and for the transfer of waste, toxins and excess water to take place. The source can include multiple sterile dialysate solution bags.

APD machines pump spent dialysate from the peritoneal cavity, though the catheter, and to the drain. As with the manual process, several drain, fill and dwell cycles occur during dialysis. A "last fill" occurs at the end of APD and remains in the peritoneal cavity of the patient until the next treatment.

In any of the above modalities, entrained air and other gases are a concern. Entrained air can cause inaccuracies when pumping dialysate for either PD or HD. Entrained air entering a patient's peritoneum during PD can cause discomfort. Entrained air entering a patient's bloodstream during HD can have severe consequences. Accordingly, a need exists to provide an apparatus that ensures that entrained air is removed from dialysate or blood prior to delivering such fluids to the patient.

SUMMARY

The present disclosure relates to air and gas removal for dialysis systems. The structures disclosed herein can be performed in any type of peritoneal dialysis treatment or blood dialysis treatment such as hemodialysis, hemofiltration, hemodiafiltration and continuous renal replacement therapy.

The embodiments below are disclosed in connection with a dialysis disposable that is loaded into a dialysis instrument. The dialysis disposable is part of an overall dialysis set which can include one or more supply bag, one or more drain bag, a heater bag and associated tubing connecting the bags to the dialysis disposable. The user places the dialysis disposable within the dialysis instrument for therapy. The dialysis disposable can include one or more pump chamber, flow path and/or valve chamber. The dialysis instrument includes one or more pump actuator that actuates the pump chamber of the disposable. The dialysis instrument also includes one or more valve actuator that actuates the valve chamber of the disposable. The disposable can also include a fluid heating pathway that operates with a fluid heater of the dialysis instrument.

While the air traps are shown herein in connection with a disposable set described below, the separation chambers are alternatively stand-alone apparatuses that operate independent of the disposable. Further, the present disclosure mainly discusses air but other gases can also be present and therefore the present air separation chambers can also trap these gases. In PD for example, gases from the patient can become entrained in fluid being pumped form the system. Also, gases from dialysate concentrate, such as bicarbonate can become entrained in fresh dialysate. It is expressly contemplated for the air separation chambers of the present disclosure to remove these additional types of gases.

As mentioned above, air in dialysate or dialysis fluid as well as air in blood needs to be removed before any of these fluids are either delivered to a dialyzer or patient. Air can be present in the system via air trapped in supply bags, air trapped in the tubes leading from the supply bags to the disposable, air not completely primed from the disposable itself and air that is released from solution when the dialysis fluid is heated. Air can also signal a leak in the disposable unit.

The air traps discussed below are shown generally in connection with a dialysis fluid, such as dialysate, having entrained air. It should be appreciated however that the embodiments are applicable equally to the removal of air from blood pumped from a patient to a hemodialyzer or hemofilter. As used herein, the term dialysis fluid includes, without limitation, mixed dialysate, mixed infusate, mixed replacement fluid, concentrated components of any of these, and blood.

In one embodiment, the disposable defines an air separation chamber that has a fluid inlet and a fluid outlet. An inlet valve and an outlet valve are paired with the fluid inlet and fluid outlet of the air separation chamber, respectively. The air separation chamber also includes an air vent outlet, which is in fluid communication with one or more air vent valve. The air removed from fluid in the air trap is sent to atmosphere or to a drain, for example, whichever is desired.

In one embodiment, the air separation chamber is configured with respect to the other components of the disposable such that when the disposable is loaded into the dialysis instrument, at least one of the fluid inlet and fluid outlet are located towards a bottom or bottom wall of the air separation chamber, while the air outlet is located at or near the top of the dialysis instrument. The inlet and out are likely located below the air outlet. Such configuration allows buoyancy forces to lift air bubbles from the dialysis fluid to the top of the air separation chamber for venting.

The dialysis disposable in one embodiment includes a cassette having a rigid portion, which can be a hard plastic. The rigid portion is formed to have pump chambers (e.g., for diaphragm pumps) or pump tubing (for peristaltic pumping), fluid pathways and valve chambers. The rigid portion also defines some or all of the air separation chamber. It is contemplated that the disposable cassette will have flexible sheeting welded to one or both sides of the rigid portion of the cassette. The flexible sheeting allows a pneumatic or mechanical force to be applied to the pump chambers (e.g., diaphragm) and valve chambers to operate those chambers. It is also contemplated that at least one outer surface of the air separation chamber consume a portion of one or both flexible sheets.

The disposable cassette can have a base wall or mid-plane that divides the cassette into first and second sides. For example, in one embodiment the flow paths are provided on one side of the disposable cassette (one side of the base wall), while the pump and valve chambers are provided on the other side of the disposable cassette. The air separation chamber in one embodiment is provided on either the first or second side, whichever is more convenient. Here, the air separation chamber has one side surface that is the rigid mid-plane and a second side surface that is cassette sheeting, which is welded to an air separation chamber inlet wall, an air separation chamber outlet wall, an air separation chamber top wall and an air separation chamber bottom wall, which each extends from and is formed with the mid-plane of the rigid portion.

It is expressly contemplated however to make the outer wall of the disposable cassette of a rigid material as opposed to cassette sheeting. For example, a rigid piece of plastic could be welded, adhered or otherwise bonded sealingly to the air separation walls extending from the mid-plane of the rigid portion.

In still a further alternative embodiment, the mid-plane is not present within the air separation chamber, and the air separation chamber is bonded on two sides by flexible sheeting. Still further alternatively, the mid-plane is not provided, however the outer walls of the air separation chamber are rigid and adhere to the top, bottom, inlet and outlet walls via a suitable sealing process.

The air separation chamber in one embodiment includes an inlet that causes the dialysis fluid to fall from the inlet, like a fountain, into a pool of dialysis fluid which degasses before flowing out a bottom of the air separation chamber. The air separation chamber provides a dual prong attack to pull gas bubbles from air. First, the fountain-like inlet of the dialysis fluid causes the fluid to separate, exposing a large surface area of fluid to air and mixing the dialysis fluid to help separate bubbles from the fluid. Second, the pooling of the dialysis fluid enables buoyancy forces to push air bubbles out of the fluid.

In one implementation shown below, dialysis fluid flows upwardly through a centrally located fluid inlet. The fluid bubbles out of the inlet, pools at a level below the inlet and exits one or more outlet located at the bottom of the air separation chamber (when placed in an operating position).

In another implementation shown below, dialysis fluid flows upwardly through an inlet located at one side of the air separation chamber. The fluid bubbles out of the inlet, pools at a level below the inlet and exits at an outlet located at the bottom and opposite side of the air separation chamber (when placed in an operating position). A ramped surface is provided from the outlet located at one side of the chamber to the inlet located at the other side of the chamber.

In a further implementation shown below, dialysis fluid flows horizontally out of an inlet located at one side of and nearer to the top of the air separation chamber. A splash wall is provided near the inlet opening. The fluid flows out of the inlet, hits the splash wall, and pools at a level below the inlet, and exists at an outlet located at the bottom and same side of the air separation chamber as the inlet (when placed in an operating position). The bottom of the chamber can be ramped downwardly towards the outlet.

In another embodiment, the air separation chamber combines buoyancy forces with a cyclone formed within the chamber to remove gas bubbles upwardly from within a center of the cyclone formed in the air separation chamber. In an embodiment, fluid enters the air trap eccentrically and spirals downwardly to the outlet, and air bubbles are collected in the center of the cyclone and degassed at the top of the chamber.

The cyclone is formed in one embodiment by staggering ramps within a substantially rectangular chamber formed in the air separation chamber. The ramps can form central openings allowing gas to proceed up the middle of the cyclone. The ramps are alternatively partitioned such that the dialysis fluid swirls back and forth from side to side within the cassette and such that a gap is left between the partitioned ramps for air bubbles to rise. Two such partitioned spiraling sets of ramps can be provided to form a pair of intertwined spiral flow paths having a central air removal channel in the shared center of the flow paths.

Further alternatively, the air separation chamber can include sides made of flexible sheeting as mentioned above which can be sucked against chamber halves formed in the dialysis instrument. The chamber halves can be configured to cooperate with sides of the dialysis cassette that are also shaped to form, with the instrument chamber halves, a relatively large elliptical or oval shaped volume that is conducive to forming the spiral or cyclone path. Here, the dialysis fluid spins from top to bottom of the air separation chamber, allowing air to degas up the middle of the cyclone.

In a further alternative embodiment, the air separation chamber uses a venturi effect to pull air out of the dialysis fluid. Here, the inlet of the air separation chamber nozzles down to a neck. An air trap or collection bulb is placed at the neck. The fluid accelerates when it reaches the neck and flows by the air trap or collection bulb which generates a vacuum in the bulb, pulling air from the dialysis fluid.

In yet another alternative embodiment, the air separation chamber is configured to force dialysis fluid through a narrow fluid film-forming section which induces a narrow or film-like flow of the dialysis fluid. The film-like flow spills into a pool of fluid. The film increases the surface area of the fluid that is exposed to air, promoting removal of air from the fluid to atmosphere. Air that reaches the pool is forced from the pool via buoyancy.

For any of the embodiments described herein, the air separation chamber can provide a filter or mesh for catching particles. The filter or mesh can also be a collection point for collecting air. The cassette having the air separation chamber can in one embodiment include indents or alignment apparatuses that ensure that the cassette is aligned properly within the dialysis instrument so that a sensor will sense a desired portion of the cassette. For example, it is contemplated to measure the pressure or level of air in the air separation chamber to know when to open a vent valve to allow air in the chamber to depressurize. The indents or alignment apparatuses mate with corresponding apparatuses located on the dialysis instrument to ensure that the proper air separation area of the cassette is aligned with the pressure or level sensor.

It is accordingly an advantage of the present disclosure to provide improved air separation chambers for the removal of air from the dialysis fluid or blood flowing through a disposable dialysis fluid apparatus.

Additional features and advantages are described herein, and will be apparent from, the following Detailed Description and the figures.

BRIEF DESCRIPTION OF THE FIGURES

FIGS. 8A and 8B are elevation and top views, respectively, of still another embodiment of a disposable-based dialysis fluid air separation chamber configured to cause a cyclone flow of dialysis fluid within the air separation chamber.

FIG. 10 is an elevation view of an embodiment of a disposable-based dialysis fluid air separation chamber configured to cause a film flow of dialysis fluid within the air separation chamber.

DETAILED DESCRIPTION

Figure 1:
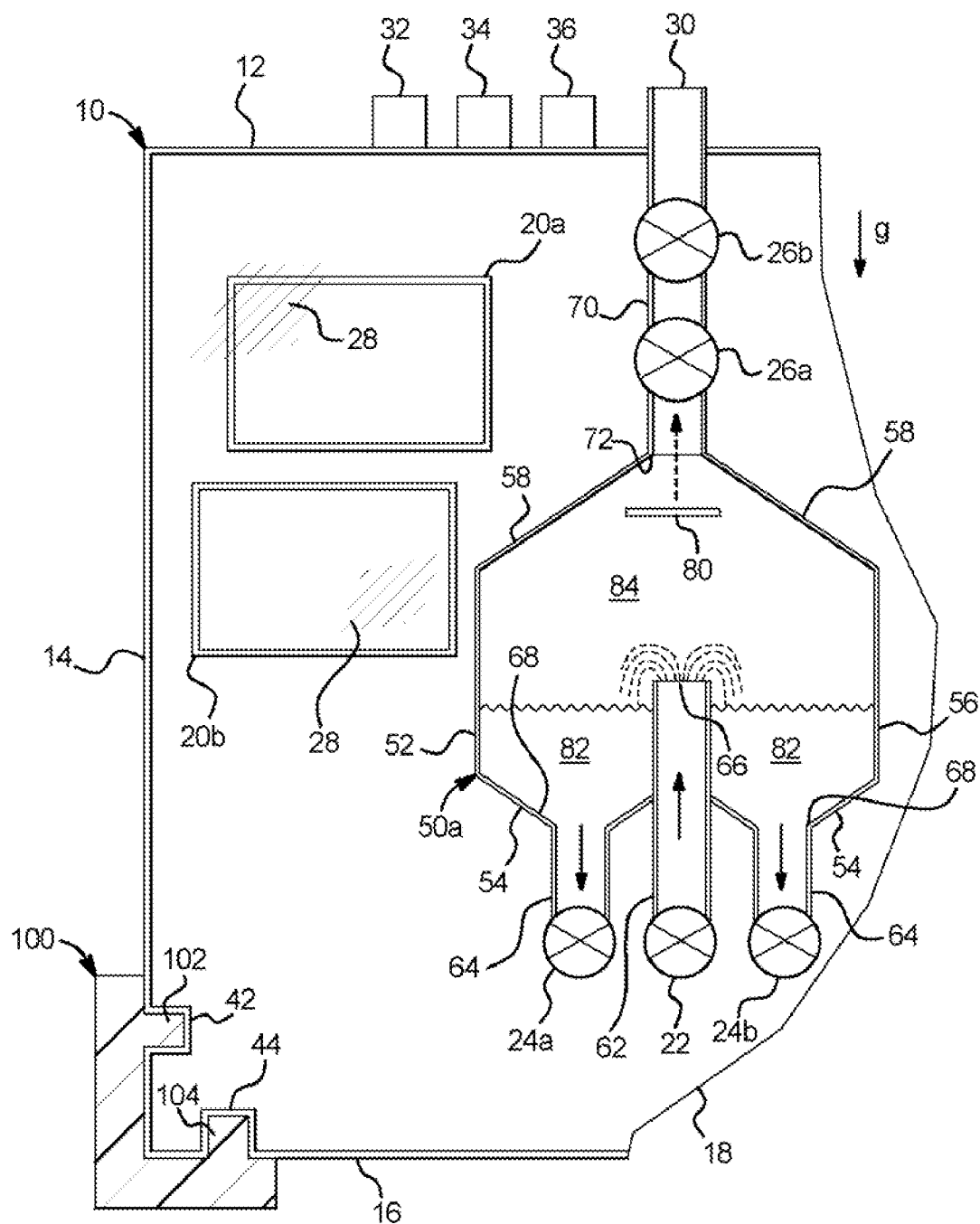
FIG. 1 is an elevation view of one embodiment of a disposable-based dialysis fluid air separation chamber using a low pressure inlet flow of dialysis fluid to the air separation chamber.

Referring now to the drawings and in particular to FIG. 1, dialysis disposable, e.g., cassette 10, having air trap 50 illustrates one embodiment of the present disclosure (air trap 50 refers generally to air traps 50a to 50j discussed herein). While air traps 50 are shown herein in connection with a disposable set described below, the separation chambers are alternatively stand-alone apparatuses that operate independent of the disposable cassette.

Dialysis cassette 10 is operable with any type of dialysis instrument such as a peritoneal dialysis instrument, hemodialysis, hemofiltration, hemodiafiltration or continuous renal replacement therapy instrument. Dialysis cassette 10 can hold a dialysis fluid such as dialysate or blood. The dialysis fluid can be premixed or cassette 10 can carry a component of dialysate such as a dialysate concentrate.

Dialysis cassette 10 in one embodiment is part of a disposable set which includes one or more supply bag, a drain bag, a heater bag, and tubing running from those bags (not illustrated) to dialysis cassette 10. Dialysis cassette 10 in one embodiment is disposable, however, dialysis cassette 10 can be cleaned for multiple uses in which the air traps described herein are used multiple times. Dialysis cassette 10 includes a rigid portion have a cassette top wall 12, a cassette side wall 14 and a cassette bottom wall 16. Suitable materials for the rigid portion include polyvinyl chloride ("PVC"), acrylic, ABS, polycarbonate and polyolefin blends. The rigid portion of cassette 10 also includes a base wall or mid-plane 18 which separates cassette 10 into first and second sides.

The side of mid-plane 18 illustrated in FIG. 1 includes pump chambers 20a and 20b which here are part of a pneumatically and/or electromechanically operated diaphragm pump. Alternatively, cassette 10 includes peristaltic pumping tubes that operate with a peristaltic pump actuator of the dialysis instrument. Cassette 10 also includes valve chambers, such as air separation inlet valve chamber 22, air separation outlet valve chambers 24a and 24b and air separation air vent valve chambers 26a and 26b. The valve chambers can also be pneumatically and/or electromechanically operated.

The other side of cassette 10 divided by mid-plane 18 (not illustrated) can include flow paths for example and/or other valve chambers and/or pump chambers. It should be appreciated that cassette 10 can have different structural layouts without affecting the performance air separation chamber 50. Air separation chamber 50 can be located on either side of mid-plane 18 for space purposes or other reasons related to component layout.

In the illustrated embodiment, the rigid portion of cassette 10 defines the wall or walls of pump chambers 20a and 20b that operate with a flexible cassette sheeting 28 which is welded, heat sealed or solvent bonded to rigid walls 12, 14, 16, etc., of the rigid portion of cassette 10. Suitable cassette sheeting 28 includes polyvinyl chloride ("PVC"), polypropylene/polyethylene blends, polypropylene or Kraton blends, polyester, polyolefin, and ULDPE. The suitable PVC sheeting can include, for example, monolayer PVC films, non-DEHP PVC monolayer films, monolayer non-PVC and multilayer non-PVC films (wherein different layers are chosen to provide strength, weldability, abrasion resistance and minimal "sticktion" to other materials such as rigid cassette materials). Multiple layers can be co-extruded or laminated together.

Cassette sheeting 28 is also used to open and close valve chambers, such as chambers 22, 24a, 24b, 26a and 26b. The dialysis instrument includes a processor and memory that operate a program which controls when valve chambers 22, 24a, 24b, 26a and 26b are opened or closed. For example, inlet and outlet valve chambers 22, 24a and 24b can be sequenced during priming to fill air separation chamber 50. Inlet and outlet valve chambers 22, 24a and 24b are open during dialysis fluid delivery and/or blood pumping to remove air from those fluids. While inlet and outlet valve chambers 22, 24a and 24b are shown directly in front of and behind the air separation chambers, it is also contemplated to move one or both the inlet and outlet valves 22, 24a and 24b further away from the air separation chamber. One or both of inlet and outlet valve chambers 22, 24a and 24b can be configured to control flow to multiple places within cassette 10, including the air separation chamber.

The memory and processing are also programmed to operate vent valve chambers 26a and 26b so as to remove air from the air separation chamber in a manner that does not affect the sterility of the dialysis fluid flowing through cassette 10. To this end, the processing and memory can operate with an air pressure signal from a pressure sensor (or level signal from a level sensor) monitoring the pressure of air (level of fluid) within the air separation chamber. The signal is monitored to determine when to perform the air purge valve sequence of valve chambers 26a and 26b. Alternatively, the processing and memory are programmed to perform the valve sequence for valve chambers 26a and 26b at set intervals.

Cassette 10 in FIG. 1 also includes a plurality of rigid ports extending from one of the walls such as cassette top wall 12. In the illustrated embodiment, cassette 10 includes a vent port 30, which operates with vent valve chambers 26a and 26b and air separation chamber 50. Cassette 10 also includes other ports, such as one or more fluid supply port 32, a drain port 34, a to- or from-heater port 36 and other ports, such as patient port and heater bag port.

Vent port 30 can vent air from air separation chamber 50 to atmosphere or to drain in different embodiments. Cassette 10 can include other apparatuses (not illustrated) such as pressure sensing areas, heater flow path areas, and additional pumping areas such as heparin and/or saline pumping areas.

Cassette 10 further includes alignment notches 42 and 44 that mate with alignment projections 102 and 104 of dialysis instrument 100 when cassette 10 is loaded into instrument 100. Mating apparatuses 42/102 and 44/104 (and potentially others, not limited to two) ensure that cassette 10 is aligned correctly with corresponding actuators, sensors and other hardware located within instrument 100. For example, instrument 100 can include a level sensor or pressure sensor to sense when air vent valves should be sequenced to vent air from the air separation chamber. Mating apparatuses 42/102 and 44/104 ensure that an air collection portion of the chamber is aligned properly with the pressure chamber or that cassette 10 is positioned so that the level sensor reads the level of dialysis fluid correctly.

FIG. 1 shows one embodiment of the air separation chamber or air trap of the present disclosure, namely, air separation chamber 50a. Air separation chamber 50a includes a first side wall 52, a bottom wall 54, an second side wall 56 and a top wall 58.

In general, walls 52 to 58 can extend from mid-plane 18 such that mid-plane 18 forms one of the broad sides of air separation chamber 50. Alternatively, mid-plane 18 extends along the outside of walls 52 to 58 but not inside air separation 50, such that walls 52 to 58 extend the entire width of cassette 10. Here, both broad surfaces of air separation chamber 50 can be made of flexible sheeting 28. Alternatively, one or both of the broad surfaces of air separation chamber 50 are made of the rigid material, wherein sheeting 28 is then welded to the rigid broad surfaces of air separation chamber 50. For example, the profile shape of air separation chamber 50 can be welded or solvent bonded to walls 52 to 58. Thereafter, the sheeting is welded or solvent bonded to the edges of the rigid profile sides of air separation chamber 50. Further, in the case in which mid-plane 18 forms one of the broad sides of air separation chamber 50, the outer broad surface of air separation 50 can be flexible sheet 28 or a rigid piece that is welded or solvent bonded to walls 52 to 58.

Inlet valve chamber 22 opens and closes an inlet pathway 62, while outlet valve chambers 24a and 24b open and close outlet pathways 64. Inlet pathway 62 communicates with air separation chamber 50 via inlet 66 which is formed in bottom wall 54. Outlet pathways 64 communicate with air separation chamber 50 via outlets 68 also formed in wall 54 of air separation chamber 50. It should be appreciated that while valve chambers 22, 24a and 24b are shown as inlet and outlet valves, respectively, each valve chamber can be either an inlet or outlet valve, e.g., for priming purposes each valve chambers 22, 24a and 24b can be an inlet valve chamber that primes air removal chamber 50 up to vent line 70.

Vent valves 26a and 26b open and close a vent line 70. Vent line 70 communicates with vent port 30 and with air separation chamber 50 via a vent outlet 72 formed in top wall 58 of air separation chamber 50. Dual vent valves 26a and 26b allow the processing and memory of the dialysis instrument to isolate a slug of air in vent line 70 before vent valve 26b is opened, allowing the air to escape via vent port 30 to atmosphere or drain. In the programmed sequence, with vent valve 26b closed, vent valve 26a is opened allowing vent line 70 to become pressurized with air. Once line 70 becomes pressurized, valve 26a is closed and valve 26b is opened, relieving the pressure in vent line 70.

With air separation chamber 50a, inlet pathway 62, outlet pathways 64 and vent line 70 are at least substantially parallel to each other. Walls 52 and 56 are at least substantially parallel to each other. Bottom wall 54 and top wall 58 are angled to smooth flow and to reduce trapped air. Air separation chamber 50a can be configured differently. For example, the profile shape can be alternatively substantially rectangular, and the inlet pathway 62 and outlet pathways 64 can alternatively extend to side walls 52 and 56. A single outlet 64 and valve chamber 24a can be provided instead of two dialysis fluid outlets.

Inlet pathway 62 of air separation chamber 50a extends upwardly into the chamber when cassette 10 is placed into the dialysis instrument. Dialysis fluid flows against gravity g from the opening 66 of inlet pathway 62 into the air collection area 84 of the air separation chamber. A splash plate 80 is provided to prevent the dialysis fluid from splashing up into vent line 70. The dialysis fluid spills over from the top of inlet pathway 62 into dialysis fluid pool 82. The dialysis fluid flows from pool 82, through one or more outlet pathway 64 and to the patient or elsewhere, e.g., to a fluid heater.

Air separation chamber 50a promotes air separation through multiple modes. First, forcing the dialysis fluid to flow over inlet opening 66 of inlet tube 62 separates the dialysis fluid, exposing more of its surface area to the atmosphere. Exposing fluid surface area also exposes gas bubbles trapped within the fluid, allowing the bubbles to escape to air collection portion 84. Second, once the dialysis fluid falls into fluid pool 82, buoyancy forces in the pool push remaining air bubbles up to air collection portion 84.

Figure 2:
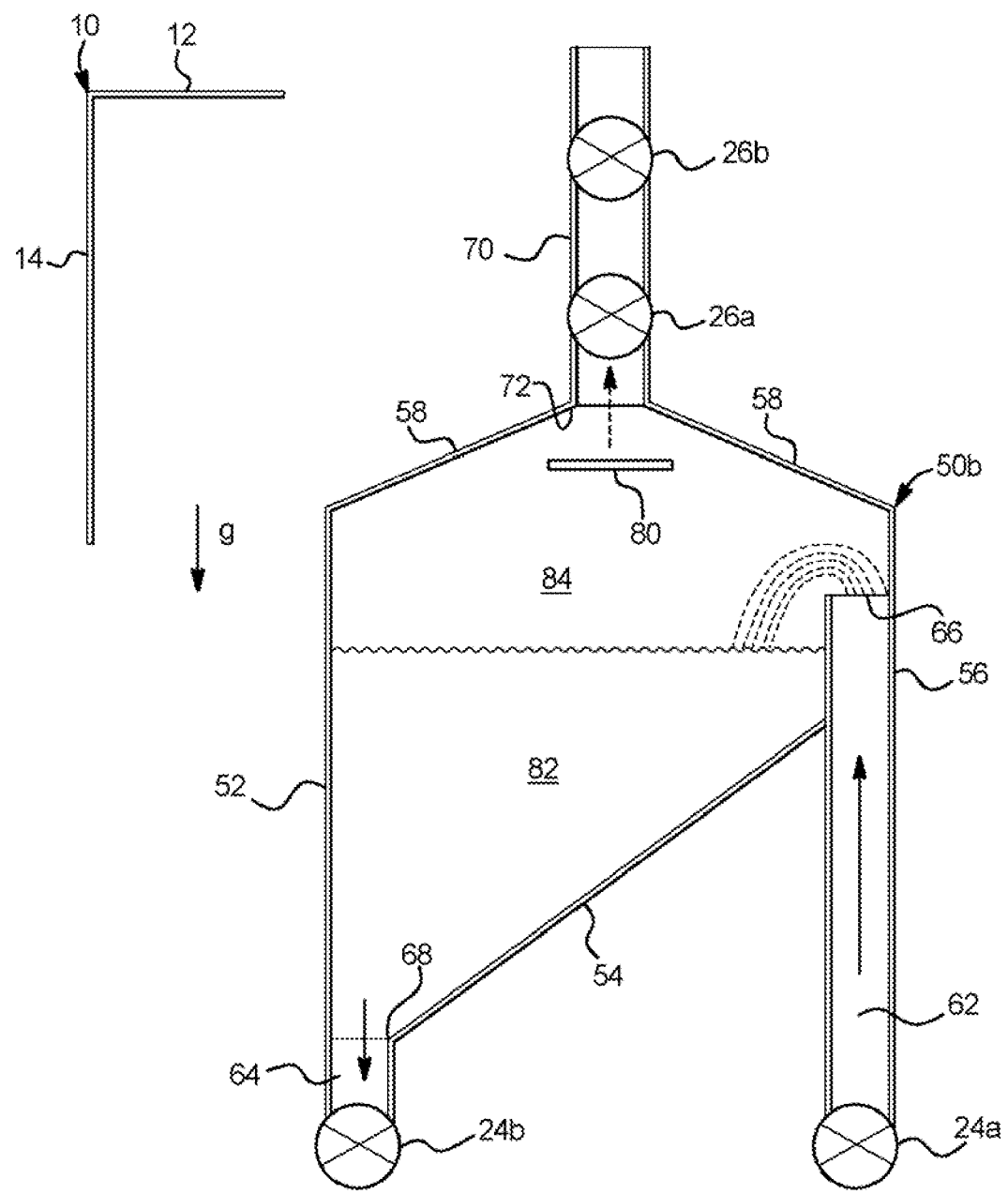
FIG. 2 is an elevation view of another embodiment of a disposable-based dialysis fluid air separation chamber using a low pressure inlet flow of dialysis fluid to the air separation chamber.

Air separation chamber 50b operable with cassette 10 of FIG. 2 illustrates another splash and pool embodiment of the present disclosure. With air separation chamber 50b, inlet pathway 62, outlet pathways 64 and vent line 70 are again at least substantially parallel to each other. Walls 52 and 56 are also at least substantially parallel to each other. Top wall 58 is angled to smooth flow and reduce the possibility of trapping air. Bottom wall 54 is angled from inlet 62 to outlet 64 to allow gravity g to create a generally right-to-left, downward flow. Air separation chamber 50b can be configured differently, for example, the profile shape can be alternatively substantially rectangular, or the inlet pathway 62 and outlet pathway 64 can alternatively extend to side walls 52 and 56.

Inlet pathway 62 of air separation chamber 50b extends upwardly into and along the right side of the chamber 50a when cassette 10 is placed into the dialysis instrument. Dialysis fluid flows against gravity g from the opening 66 of inlet pathway 62 into the air collection area 84 of the air separation chamber. A splash plate 80 is provided to prevent the dialysis fluid from splashing up into vent line 70. The dialysis fluid spills over from the top of inlet pathway 62 and into dialysis fluid pool 82. The dialysis fluid flows from pool 82, through outlet pathway 64 and to the patient or elsewhere.

Air separation chamber 50b, like chamber 50a, promotes air separation by flowing the dialysis over inlet opening 66, separating the dialysis fluid, exposing more of its surface area to the atmosphere and exposing gas bubbles trapped within the fluid to atmosphere. Moreover, once the dialysis fluid falls into fluid pool 82, buoyancy forces in the pool push remaining air bubbles up to air collection portion 84.

Figure 3:
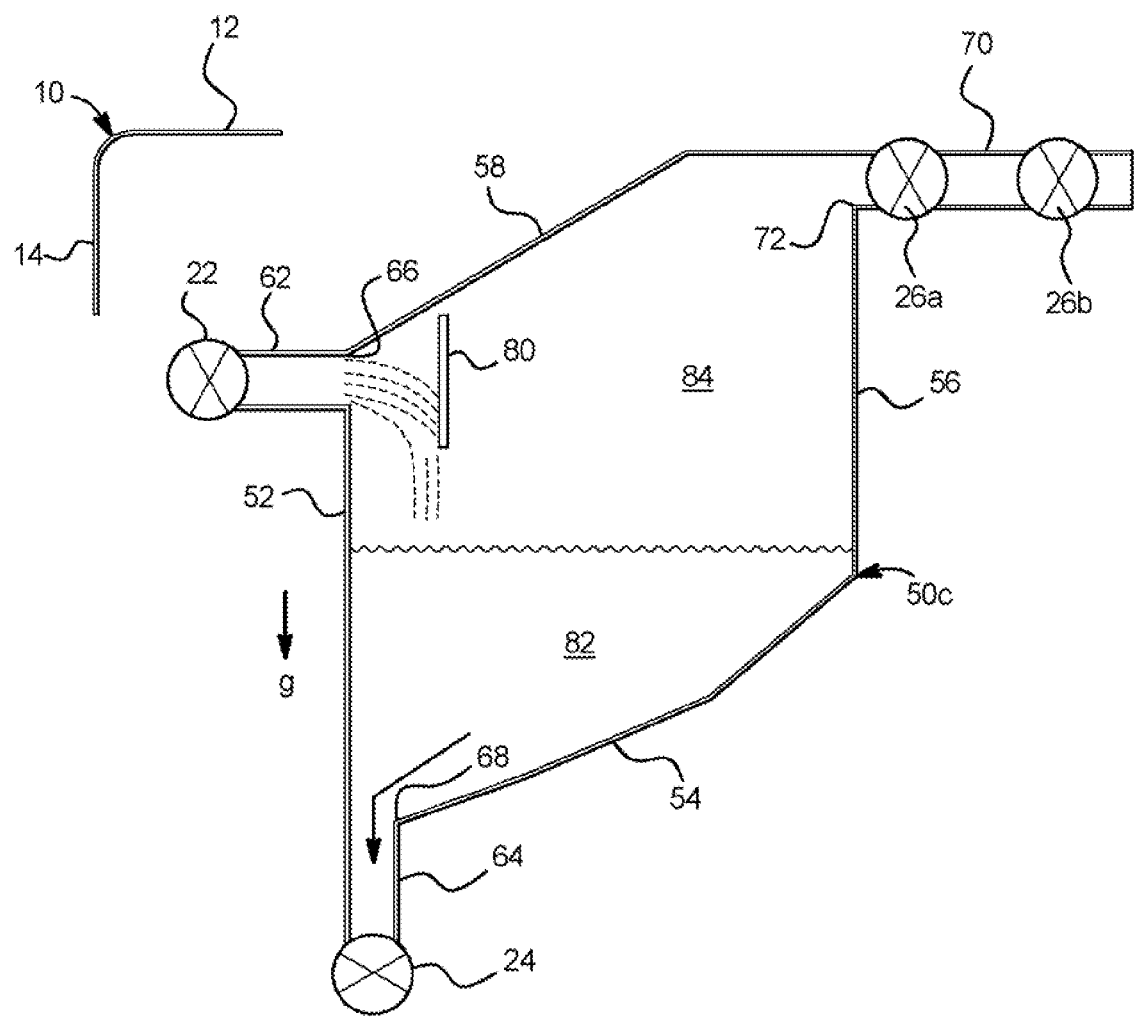
FIG. 3 is an elevation view of a further embodiment of a disposable-based dialysis fluid air separation chamber using a low pressure inlet flow of dialysis fluid to the air separation chamber.

Air separation chamber 50c operable with cassette 10 of FIG. 3 illustrates a further splash and pool embodiment of the present disclosure. With air separation chamber 50c, inlet pathway 62 and vent line 70 are again at least substantially horizontal and parallel to each other. Vent line 70 is located elevationally above inlet 62. Outlet 64 is disposed vertically and below inlet 62 or vent line 70. Walls 52 and 56 are also at least substantially parallel to each other. Top wall 58 is angled to smooth flow and to reduce trapped air. Bottom wall 54 is angled from second side 56 to outlet 64 to allow gravity g to create a generally right-to-left, downward flow.

Dialysis fluid flows horizontally through inlet pathway 62 of air separation chamber when cassette 10 is placed into the dialysis instrument. Dialysis fluid flows from the opening 66 of inlet pathway 62 into the air collection area 84 of the air separation chamber. The dialysis fluid hits a splash plate 80 which breaks apart the dialysis fluid. The dialysis fluid spills down from splash plate 80 into dialysis fluid pool 82. The dialysis fluid flows from pool 82, through outlet pathway 64 and to the patient or elsewhere.

Air separation chamber 50c, like chambers 50a and 50b, promotes air separation by impinging the dialysis fluid against splash plate 80 and separating the dialysis fluid, exposing more of its surface area to the atmosphere and thereby exposing gas bubbles trapped within the fluid to atmosphere. Moreover, once the dialysis fluid falls into fluid pool 82, buoyancy forces in the pool push remaining air bubbles up to air collection portion 84.

In the following examples the number of baffles and funnels per air separation chamber can vary from the number illustrated.

Figure 4A:
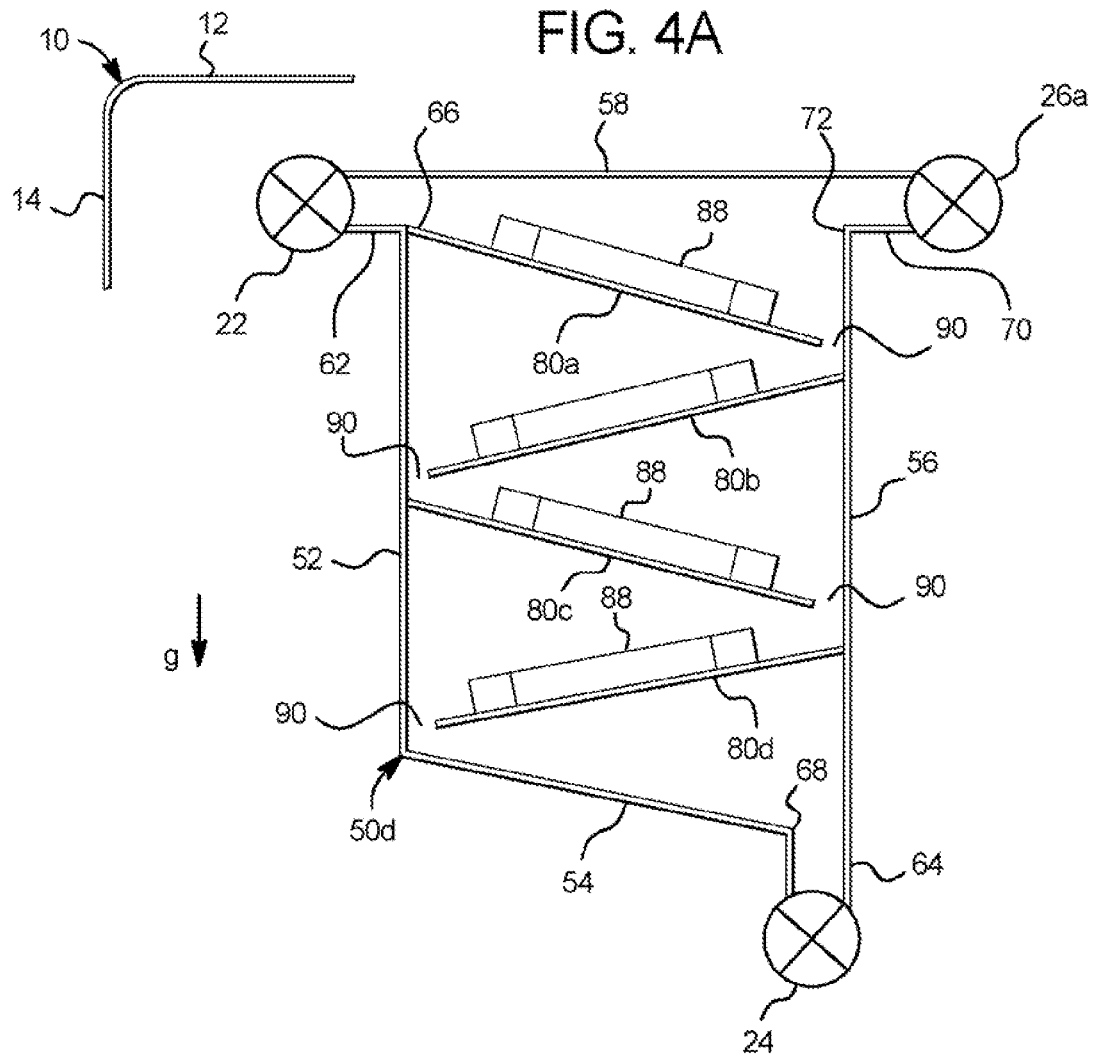
FIGS. 4A and 4B are elevation and top views, respectively, of one embodiment of a disposable-based dialysis fluid air separation chamber configured to cause a serpentine flow of dialysis fluid within the air separation chamber.
Figure 4B:
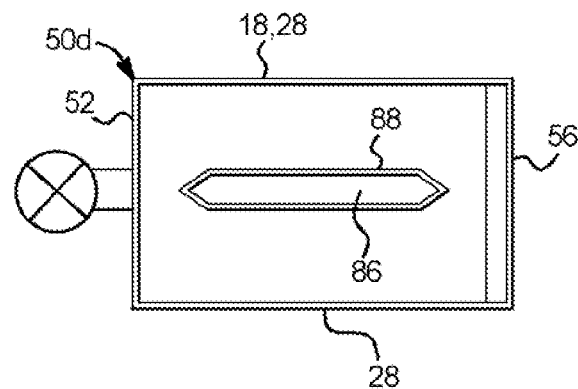

Air separation chamber 50d, operable with cassette 10 of FIGS. 4A and 4B, is one embodiment of an air separation chamber that creates a serpentine dialysis fluid flow to separate air and gas bubbles from the dialysis fluid. Inlet pathway 62 and vent line 70 are again at least substantially horizontal and parallel to or aligned with each other. Outlet 64 is disposed vertically at bottom wall 54. Walls 52 and 56 are also at least substantially parallel to each other. Bottom wall 54 is angled from first side 52 to outlet 64 to allow gravity g to create a generally left-to-right, downward flow at the bottom of air separation chamber 50d.

As seen in the top view of FIG. 4B, air separation chamber 50d can extend from mid-plane 18 or span the entire width of cassette 10. If extending from mid-plane 18, the outer surface of air separation chamber 50d can be flexible sheeting 28 (as indicated) or a piece of rigid material. If extending the entire width of cassette 10, the outer surfaces of air separation chamber 50d can be flexible sheeting 28, two pieces of rigid material, or a combination of same. Thus, depending on the configuration of air separation chamber 50d, baffles 80a to 80d together with any needed support gusseting (not shown) can extend from sidewalls 52 and 56 or from sidewalls 52 and 56 and mid-plane 18.

Air separation chamber 50d includes alternating baffles 80a to 80d. Each baffle includes or defines an air opening 86 which is surrounded by a border 88 as seen in the top view of FIG. 4B. Baffles 80a to 80d do not travel all the way from side wall 52 to side wall 56, but leave a gap 90 for the dialysis fluid to fall to the next lower baffle 80b, 80c or 80d. Borders 88 prevent, at least partially, dialysis fluid from falling though air openings 86 directly to the bottom wall 54. Borders 88 also create a central opening for air or gas to travel upwards to vent line 70. Baffles 80a to 80d increase the dialysis fluid flow path and the degassing time as the fluid flows down and back and forth along the alternating baffles. Air separation chamber 50*d* is structured to force air towards the middle of the air separation chamber, while the dialysis fluid flows around borders 88. Air separation chamber 50*d* achieves back-and-forth if not spiral fluid flow. Air separation is performed primarily through buoyancy.

Figure 5A:
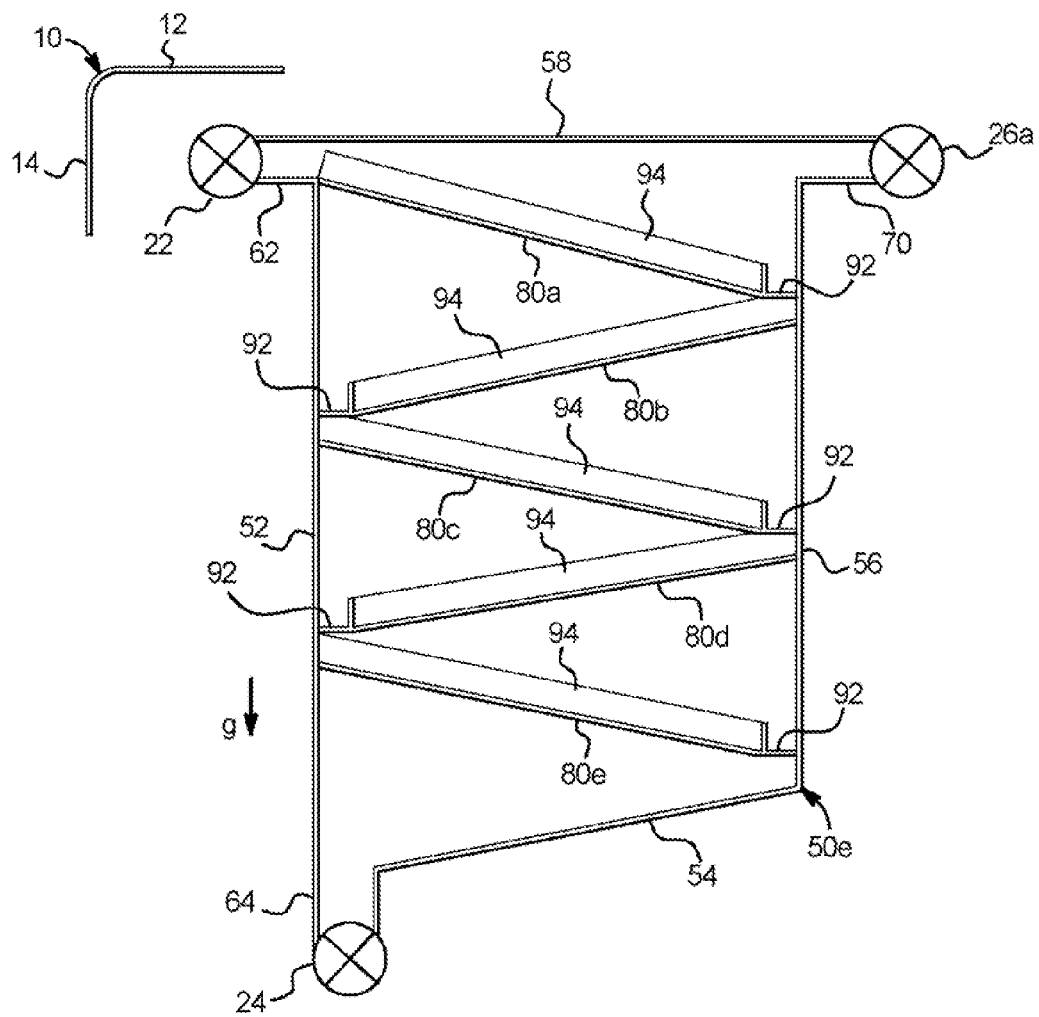
FIGS. 5A and 5B are elevation and top views, respectively, of another embodiment of a disposable-based dialysis fluid air separation chamber configured to cause a cyclone flow of dialysis fluid within the air separation chamber.
Figure 5B:
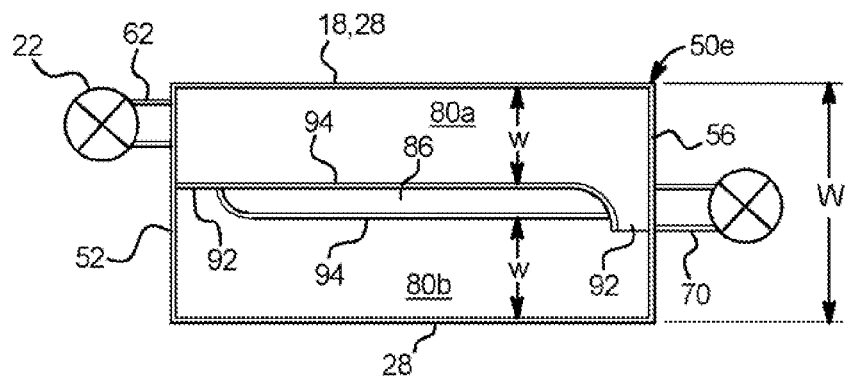

Air separation chamber 50*e*, operable with cassette 10 of FIGS. 5A and 5B, is one embodiment of an air separation chamber that creates a cyclone or spiral dialysis fluid flow to separate air and gas bubbles from the dialysis fluid. Inlet pathway 62 and vent line 70 are again at least substantially horizontal and parallel to or aligned with each other. Outlet 64 is disposed vertically at bottom wall 54. Walls 52 and 56 are also at least substantially parallel to each other. Bottom wall 54 is angled from second side 56 to outlet 64 to allow gravity g to create a generally right-to-left, downward flow at the bottom of air separation chamber 50*e*.

As seen in a top view of FIG. 5B, air separation chamber 50*e* can extend from mid-plane 18 or span the entire width of cassette 10. If extending from mid-plane 18, the outer surface of air separation chamber 50*e* can be flexible sheeting 28 (as indicated) or a piece of rigid material. If extending the entire width of cassette 10, the outer surfaces of air separation chamber 50*e* can be flexible sheeting 28, two pieces of rigid material, or a combination of same. Thus, depending on the configuration of air separation chamber 50*e*, baffles 80*a* to 80*e* together with any needed support gusseting (not shown) can extend from sidewalls 52 and 56 or from sidewalls 52 and 56 and mid-plane 18.

Air separation chamber 50*e* includes alternating baffles 80*a* to 80*e*. Each baffle has a width w of less than half a total width W of air separation chamber 50*e*. Thus, alternating pairs of baffles leave an air gap 86 between the baffles. The baffles 80*a* to 80*e* extend from side 52 to side 56 and include a turn 92 that directs fluid onto the next lower baffle 80*b* to 80*e*. Each baffle 80*a* to 80*e* includes a border 94 that bends with turn 92 and that prevents, at least partially, dialysis fluid from falling though air gap 86 directly to the bottom wall 54. Successive gaps 86 create a central opening for air or gas to travel upwards to vent line 70.

Baffles 80*a* to 80*e* increase the dialysis fluid flow path and the degassing time as the fluid flows down and back-and-forth along the alternating baffles. Air separation chamber 50*e* is structured to force air towards the middle of the air separation chamber while the dialysis fluid flows around borders 94. Air separation chamber 50*d* achieves back-and-forth and spiral fluid flow. The spiraling flow is assumed to produce a centripetal effect in which heavier fluid gravitates to the outside of baffles 80*a* to 80*e*, while lighter air separates towards the inside of the baffles and rises through gaps 86. Air separation is performed additionally through buoyancy via the elongated fluid flow path.

Figure 6A:
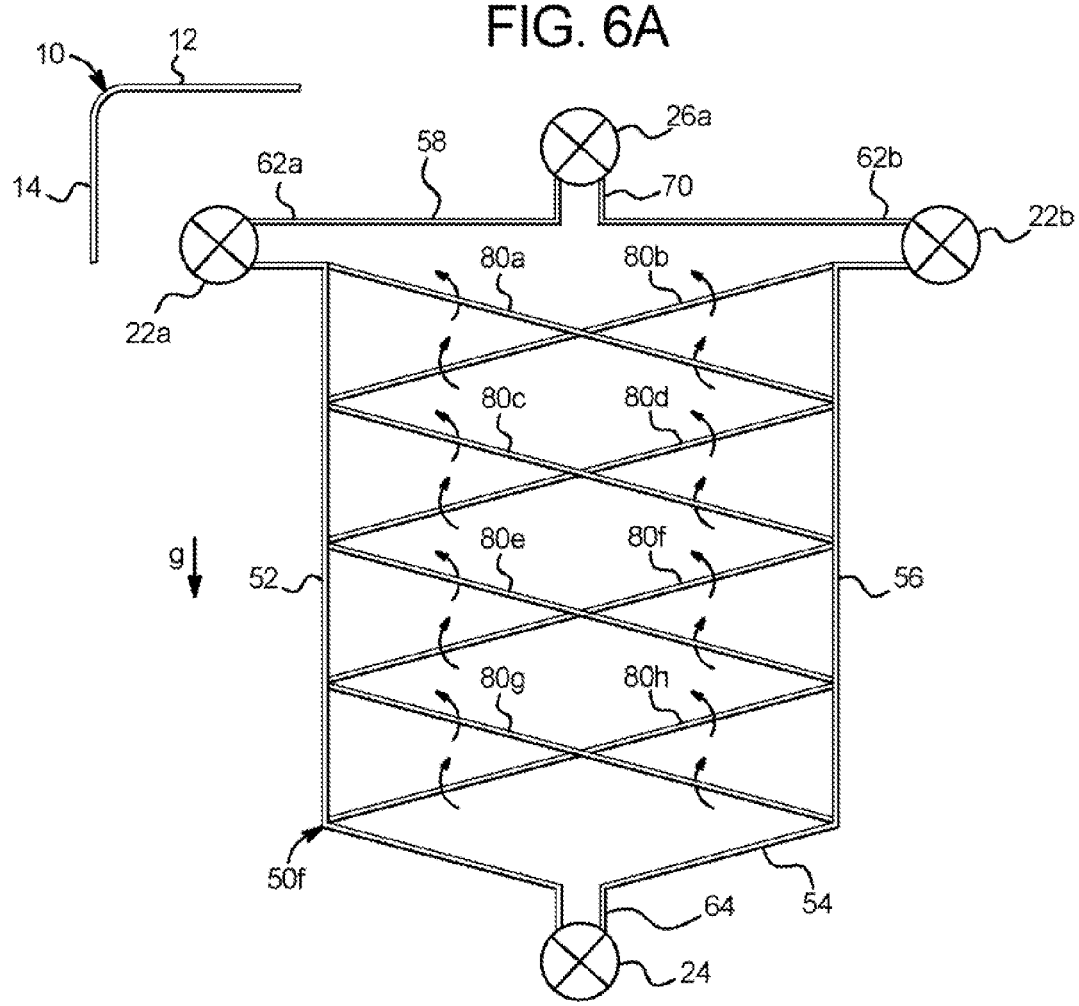
FIGS. 6A and 6B are elevation and top views, respectively, of a further embodiment of a disposable-based dialysis fluid air separation chamber configured to cause a cyclone flow of dialysis fluid within the air separation chamber.
Figure 6B:
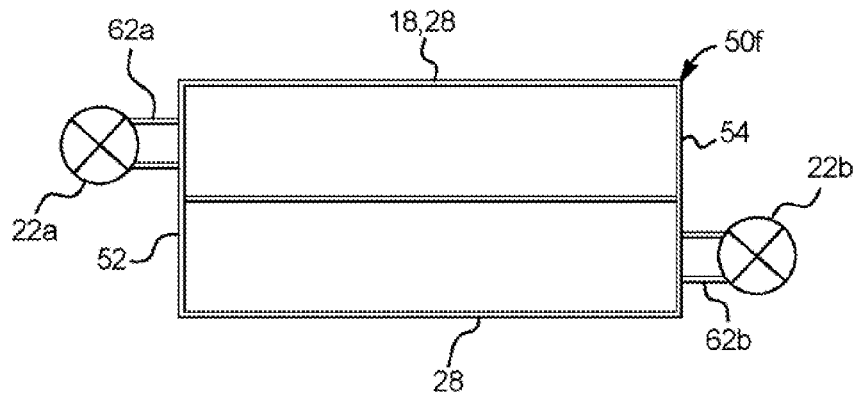

Air separation chamber 50*f*, operable with cassette 10 of FIGS. 6A and 6B, is another embodiment of an air separation chamber that creates a cyclone or spiral dialysis fluid flow to separate air and gas bubbles from the dialysis fluid. Here, chamber 50*f* includes dual inlet valve chambers 22*a* and 22*b*, which open and close dual inlet pathways 62*a* and 62*b* respectively. Chamber 50*f* creates dual spiraling paths using dual inlet pathways 62*a* and 62*b* which are least substantially horizontal and parallel to or aligned with each other. Vent line 70 is located at top wall 58 of chamber 50*f*. Outlet 64 is disposed vertically at bottom wall 54. Walls 52 and 56 are at least substantially parallel to each other. Bottom wall 54 is dual-angled from sides 52 and 56 to outlet 64 in the middle of chamber 50*f*.

As seen in a top view of FIG. 6B, air separation chamber 50*f* can extend from mid-plane 18 or span the entire width of cassette 10. If extending from mid-plane 18, the outer surface of air separation chamber 50*f* can be flexible sheeting 28 (as indicated) or a piece of rigid material. If extending the entire width of cassette 10, the outer surfaces of air separation chamber 50*f* can be flexible sheeting 28, two pieces of rigid material, or a combination of same. Thus, depending on the configuration of air separation chamber 50*f*, rear baffles 80*b*, 80*d*, 80*f* and 80*h* together with any needed support gusseting (not shown) can extend from sidewalls 52 and 56 or from sidewalls 52 and 56 and mid-plane 18. Baffles 80*a*, 80*c*, 80*e* and 80*g* extend from sidewalls 52 and 56, including any needed support gusseting (not shown).

Air separation chamber 50*f* includes dual pairs of alternating baffles 80*a* to 80*h*. One pair of alternating baffles includes baffles 80*a*, 80*c*, 80*e* and 80*g*. The other pair of alternating baffles includes baffles 80*b*, 80*d*, 80*f* and 80*h*. The two pairs spiral around one another. Each baffle has a width w of approximately or slightly less than half a total width W of air separation chamber 50*f*. The dual alternating pairs of baffles leave air paths from bottom to top indicated by the arrows in FIG. 6A. That is, air weaves up around the alternating plates on the left and right side of chamber 50*f*. The baffles 80*a* to 80*h* extend from side 52 to side 56. Turns 92 and borders 94 (as illustrated in FIGS. 5A and 5B) are not provided in the illustrated embodiment but may in some form be provided if desired.

Baffles 80*a* to 80*h* increase the dialysis fluid flow path and the degassing time as the fluid flows down and back-and-forth along the dual sets of spiraling baffles. Air separation chamber 50*f* achieves back-and-forth and spiral fluid flow. The spiraling flow is again assumed to produce a centripetal effect in which heavier fluid gravitates to the outside of baffles 80*a* to 80*h*, while lighter air separates towards the inside of the baffles. Air separation is performed additionally through buoyancy via the elongated dual fluid flow paths.

Figure 7A:
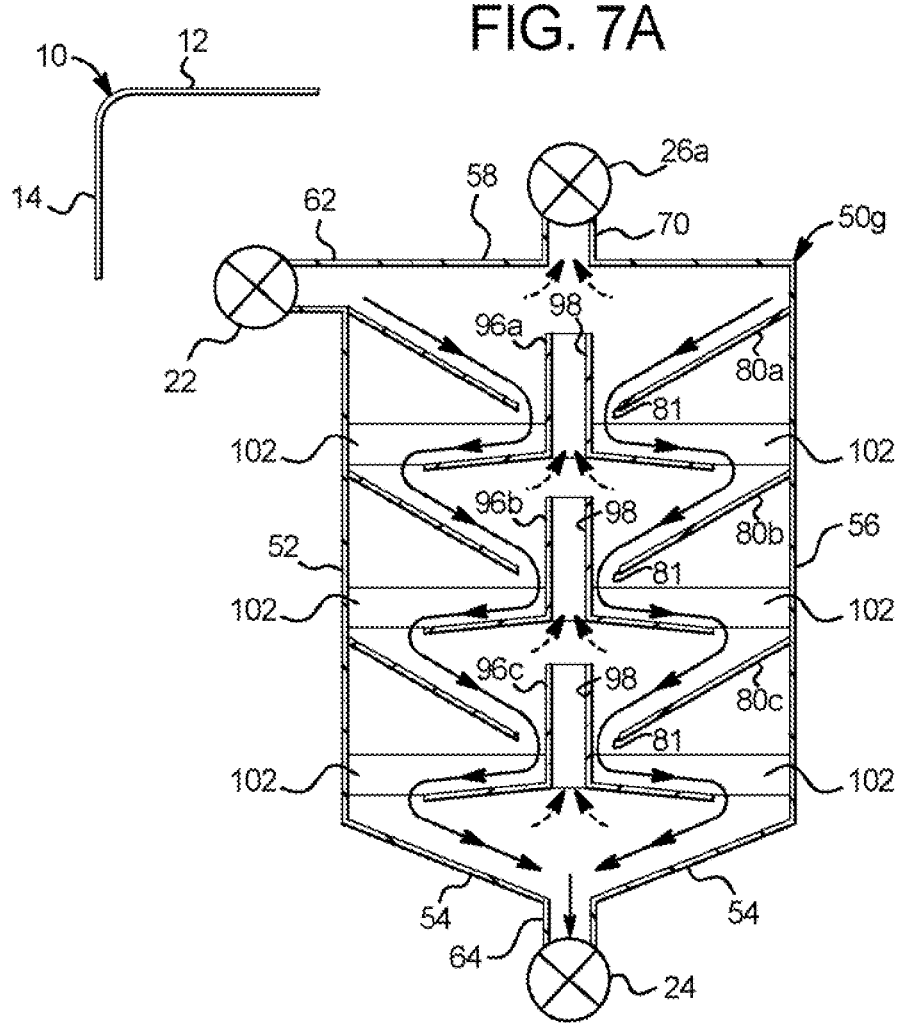
FIGS. 7A and 7B are elevation and top views, respectively, of yet another embodiment of a disposable-based dialysis fluid air separation chamber configured to cause a cyclone flow of dialysis fluid within the air separation chamber.
Figure 7B:
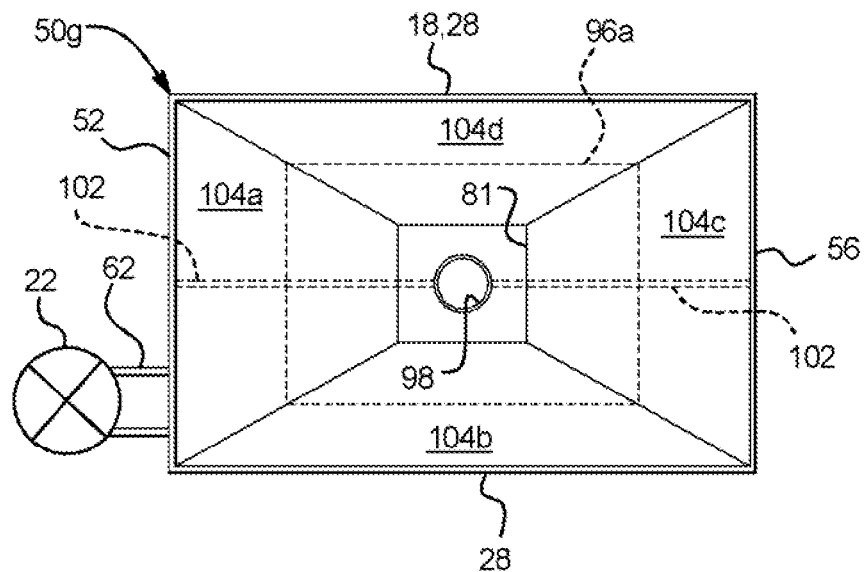

Air separation chamber 50*g*, operable with cassette 10 of FIGS. 7A and 7B, is another embodiment of an air separation chamber that creates a cyclone or spiral dialysis fluid flow to separate air and gas bubbles from the dialysis fluid. Air separation chamber 50*g* includes an upper inlet pathway 62, a vent line 70 located at top wall 58 of chamber 50*g*, and an outlet 64 disposed vertically at bottom wall 54. Walls 52 and 56 are at least substantially parallel to each other. Bottom wall 54 is dual-angled from sides 52 and 56 to outlet 64 located in the middle of chamber 50*g*.

Air separation chamber 50*g* creates a series of cyclones via mating pairs of four-sided flow funnels 80*a* to 80*c* that funnel dialysis fluid in a cyclone manner through a central hole 81 in each funnel and around an air column 98 of an associated baffle 96*a* to 96*c*. Baffles 96*a* to 96*c* receive the dialysis fluid from the central hole 81 of each funnel 80*a* to 80*c* and spread the dialysis fluid outwardly for the next funneling of the dialysis fluid. That is, baffle 96*a* funnels dialysis fluid to funnel 80*b*; baffle 96*b* funnels dialysis fluid to funnel 80*c*; and baffle 96*c* funnels dialysis fluid to bottom wall 54. The illustrated embodiment accordingly includes four separate funnels or cyclones from funnels 80*a* to 80*c* and bottom wall 54.

As seen in a top view of FIG. 7B, air separation chamber 50*g* can extend from mid-plane 18 or span the entire width of cassette 10. If extending from mid-plane 18, the outer surface of air separation chamber 50*g* can be flexible sheeting 28 (as indicated) or a piece of rigid material. If extending the entire width of cassette 10, the outer surfaces of air separation chamber 50*g* can be flexible sheeting 28, two pieces of rigid material, or a combination of same. Thus, depending on the configuration of air separation chamber 50g, funnels 80a to 80c and baffles 96a to 96c together with any needed support gusseting (not shown) can extend from sidewalls 52 and 56 or from sidewalls 52 and 56 and mid-plane 18.

In the illustrated embodiment, baffles 96a to 96c are fixed within air separation chamber 50g via support walls 102. Funnels 80a to 80c are four sided as seen in FIG. 7B, with side 104a attached to wall 52 and side 104c attached to wall 56. Sides 104b and 104d can be attached to rigid pieces (e.g., wall 104d to mid-plane 18), fixed to flexible sheets 28 or press-fit against flexible sheets. FIG. 7B also shows inlet 62 offset from center to project dialysis fluid into air separation chamber 50g at wall 104b in order to aid in the formation of the first cyclone flow through funnel 80a.

The arrangement of air separation chamber 50g produces an elongated flow path of dialysis fluid as indicated by the arrowed solid line in FIG. 7A. The fluid is forced through multiple funnels, each separating air form the fluid. Air is encouraged through a central air column formed by the series of columns 98 of baffles 96a to 96c. The spiraling flow of each funnel is again assumed to produce a centripetal effect in which heavier fluid gravitates to the outside of the funnels, while lighter air separates towards the inside of the funnels. Air separation is performed additionally through buoyancy via the elongated series fluid flow pathway.

Air separation chamber 50h, operable with cassette 10 of FIGS. 8A and 8B, is another embodiment of an air separation chamber that creates a cyclone or spiral dialysis fluid flow to separate air and gas bubbles from the dialysis fluid. Air separation chamber 50h includes un upper inlet pathway 62, a vent line 70 located at top wall 58 of chamber 50h, and an outlet 64 disposed vertically at the bottom of the air separation chamber 50h. Walls 52 and 56 as shown angle inwardly towards each other from top wall 58 in a funnel-like manner. FIG. 8A also shows that walls 52 and 56 are curved to form an oval or elliptical shape with cassette sheeting 28 when the sheeting is sucked outwardly as discussed below.

As seen in a top view of FIG. 8B, air separation chamber 50h spans the entire width of cassette 10. The outer surfaces of air separation chamber 50h are flexible sheeting 28 that is welded, adhered, solvent bonded, etc. to side walls 52 and 56. Cassette 10 is loaded into dialysis instrument 100 such that instrument chamber forming shells 106a and 106b, each having a pneumatic port 108, come into operable engagement with sheeting 28 on respective sides of air separation chamber 50h of dialysis cassette 10.

In operation, dialysis instrument 100 induces a vacuum at ports 108 of chamber forming shells 106a and 106b which pulls sheeting 28 on both sides of cassette 10 at the air separation chamber 50h against the inner walls of shells 106a and 106b. The shape of shells 106a and 106b in combination with the rounded surfaces of side walls 52 and 56 form a funneled oval or elliptical-like volume that is very conducive to forming a funneled, cyclone flow of dialysis fluid. The funneled cyclone of dialysis fluid flows from inlet 62, around and around the sheeting 28 and side walls 52 and 56 and down to outlet 24. To aid in forming the cyclone flow, inlet 62 is angled or jogged at side wall 52 in order to inject flow initially towards one of the extended sheets 28. Although not illustrated, side walls 52 and 56 can have baffles or flow directors to either obstruct the cyclone or to aid the cyclone as desired.

The arrangement of air separation chamber 50h produces an elongated flow path of dialysis fluid. Air is encouraged to move upwardly at the center of the chamber. The spiraling flow is again assumed to produce a centripetal effect in which heavier fluid gravitates to expanded sheeting 28, while lighter air separates at the center of chamber 50h. Air separation is performed additionally through buoyancy via the elongated spiraled fluid flow pathway.

Figure 9:
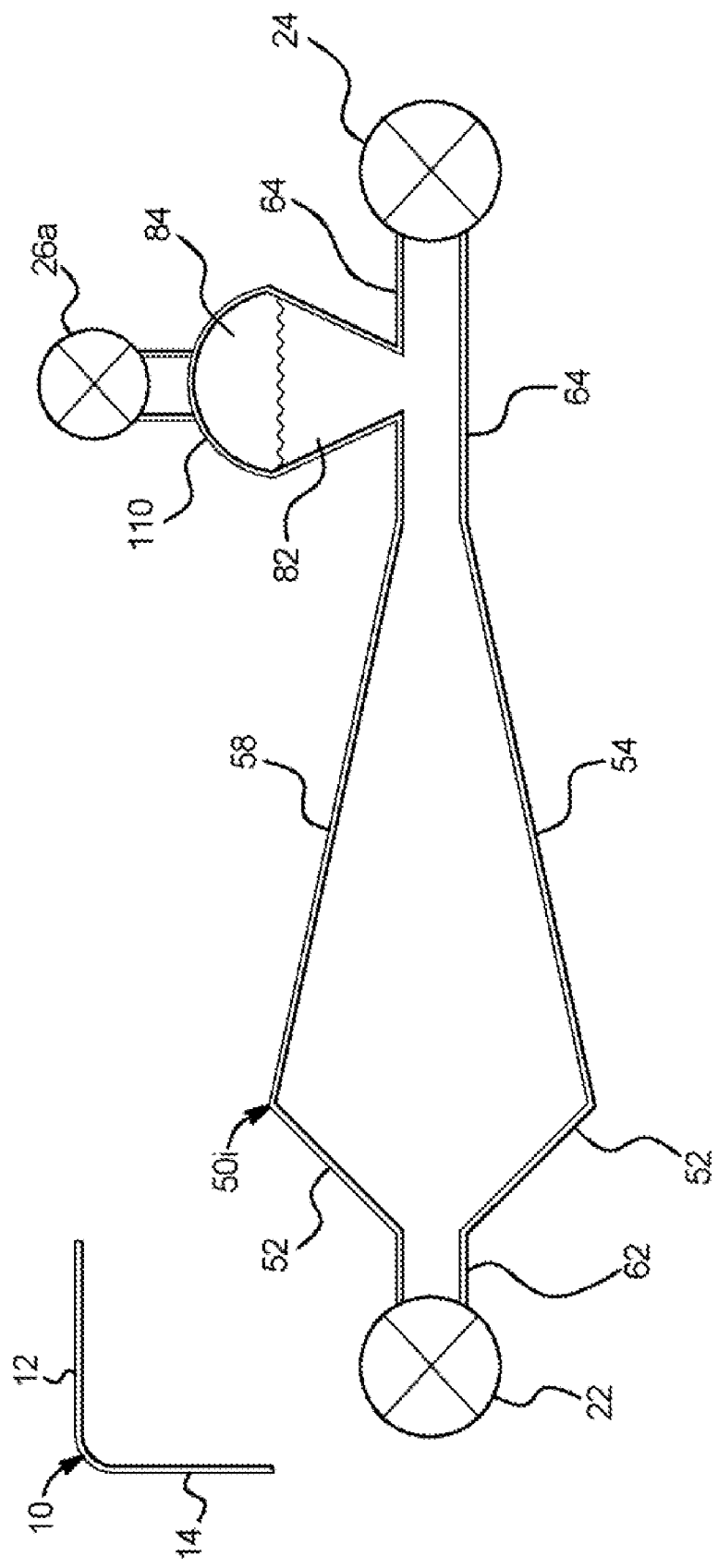
FIG. 9 is an elevation view of one embodiment of a disposable-based dialysis fluid air separation chamber configured to cause a nozzled flow leading to a vacuum separation of gas bubbles from dialysis fluid.

Air separation chamber 50i, operable with cassette 10 of FIG. 9, illustrates one embodiment of a venturi or negative pressure air separation chamber that pulls fluid under a vacuum within a closed volume "away from" entrained air, leaving air in the volume. Air separation chamber 50i includes inlet pathway 62 leading to side wall 52. Sidewall 52 is configured to expand the inlet flow of dialysis fluid to a beginning of a nozzle section of chamber 50i which is formed via top wall 58 and bottom wall 54. Walls 52 to 58 can be cylindrical or rectangular in cross-section as desired and formed of only rigid material or rigid material in combination with sheeting 28. For example, top wall 58 and bottom wall 54 can come together to form a cylindrical nozzle section. Alternatively, wall 58 and bottom wall 54 can be curved (similar to walls 52 and 56 of chamber 50h) together with nozzle and flexible sheeting side walls 28 (which can be sucked outwardly to have rounded surfaces as shown in connection with chamber 50h).

The nozzle section of chamber 50i narrows towards exit pathway 64 and exit valve 24. Narrowed exit pathway 64 is placed in fluid communication with a fixed volume bulb 110. The nozzle is constructed such that it can create a vacuum. Bulb 110 has a large enough volume so as not to necessitate drainage by a few milliliters. Conversely, the cross-section of narrowed exit pathway 64 can be rather small in relation to bulb 110. Fixed volume bulb 110 is either entirely rigid or made with sheeting that is sucked against instrument 100 to form a fixed volume. Dialysis fluid 82 that rises within fixed volume bulb 82 is subject to negative pressure due to a venturi effect of the nozzled flow through outlet 64. The negative pressure placed on fluid 82 tends to create a negative pressure in air collection portion 84 of bulb 110. The negative gage pressure has two effects on the air separation. First, such pressure will withdraw dissolved gases out of solution due to changes in the solubility and introduce the dissolved gases to the buoyant environment within bulb 110. Second, bubble of known size d1 will increase in diameter d2 (where d2>d1), allowing for faster rise times for the bubbles in the appropriate flow environment. Chamber 50i can be combined with a buoyancy pool (like below) if needed to separate risable bubbles not collected in bulb 110.

Air separation chamber 50j, operable with cassette 10 of FIG. 10, illustrates one embodiment of a film-producing/buoyancy pool air separation chamber. Here, inlet line 62 forms a thin fluid path, e.g., such as a thin liquid film that is 0.5" wide (12 mm wide) and 0.02" thick (0.5 mm wide), which produces a thin film or stream of fluid exiting opening 66 into a collection volume 112 having a liquid pool 82 and air collection area 84. Forcing the inlet to flow into a thin film or stream increases the exposed surface area of the dialysis fluid and promotes air separation as described above. The thin film will also ensure bubbles larger than the size of the film thickness will explode on their way to the collection chamber and become eliminated. The larger bubbles will be eliminated due to size exclusion and/or explosion. This will break some of the bubbles into smaller bubbles but some bubbles will explode into the free air space, becoming eliminated from the solution pool. Residual air not removed via the filming of the dialysis fluid is removed in pool 82 via buoyancy forces as described above.

It should be understood that various changes and modifications to the presently preferred embodiments described herein will be apparent to those skilled in the art. Such changes and modifications can be made without departing The invention is claimed as follows:

1. A dialysis system comprising:
    a blood disposable operable with a dialysis instrument, the blood disposable including
        a dialyzer,
        a pumping portion configured and arranged to be operated by a blood pump of the dialysis instrument, and
        an air separation chamber in fluid communication with the pumping portion, the air separation chamber including an inner surface, a blood inlet and a blood outlet, and
    wherein the pumping portion is configured to be actuated to pump blood through the dialyzer and the air separation chamber, and the air separation chamber is configured to cause the blood to spiral around the inner surface toward the blood outlet to remove air from the blood.

2. The dialysis system of claim 1, wherein the inner surface of the air separation chamber is curved.

3. The dialysis system of claim 1, wherein the inner surface of the air separation chamber is configured to promote the spiraling of the fluid.

4. The dialysis system of claim 1, wherein the fluid inlet is located near a top of the air separation chamber and the fluid outlet is located near a bottom of the air separation chamber when in operation.

5. The dialysis system of claim 1, wherein the air separation chamber further includes a vent outlet located near a top of the air separation chamber when in operation.

6. The dialysis system of claim 1, wherein the fluid inlet is disposed so as to direct the fluid in a direction promoting the spiraling of the blood.

7. The dialysis system of claim 1, wherein the air separation chamber in operation is disposed so that the blood spirals in an overall downward vertical direction, and wherein the blood inlet is disposed to direct the blood horizontally into the air separation chamber.

8. The dialysis system of claim 1, wherein the inner surface is smooth.

9. A dialysis system of claim 1, wherein the air separation chamber includes at least one internal structure configured and arranged to promote the spiraling of the blood.

10. The dialysis system of claim 1, wherein the blood disposable further includes a first blood pathway between the pumping portion and the dialyzer and a second blood pathway between the dialyzer and the air separation chamber.

11. The dialysis system of claim 1, wherein the blood disposable includes a disposable cassette having at least one rigid wall and at least one flexible sheet.

12. The dialysis system of claim 1, wherein the inner surface forms a sidewall of the air separation chamber.

13. The dialysis system of claim 12, wherein the sidewall is configured so as to cause the fluid to spiral in an overall downward vertical direction.

14. A dialysis system comprising:
    a dialysis instrument including a blood pump actuator;
    a blood disposable operable with the dialysis instrument, the blood disposable including an air separation chamber and a blood pumping portion operable with the blood pump actuator, the air separation chamber including a blood inlet and a blood outlet communicating fluidly with an inner surface of the air separation chamber, the inner surface configured to promote the spiraling of a blood to remove air from the blood.

15. The dialysis system of claim 14, wherein a fluid valve is in fluid communication with one of the blood inlet, the blood outlet or a vent of the air separation chamber.

16. The dialysis system of claim 14, wherein the blood inlet is disposed so as to direct the blood in a direction promoting the spiraling of the blood along the inner surface.

17. The dialysis system of claim 14, which includes at least one internal structure operating with the inner surface to promote the spiraling of the blood.

18. A method of removing air from a dialysis system comprising:
    introducing blood potentially containing air horizontally into an upper portion of a chamber of a blood disposable, the blood disposable including a blood pumping portion and a dialyzer;
    forcing the blood potentially containing air to spiral around the chamber from the upper portion to a lower portion of the chamber; and
    allowing the blood to exit from the lower portion of the chamber and air to migrate towards the upper portion of the chamber.

19. The method of claim 18, which includes allowing the air to migrate towards the upper portion of the chamber centrally through the spiraling blood.

20. The method of claim 18, which includes allowing air to be removed from the upper portion of the chamber.

* * * * *